United States Patent [19]

Maestrone et al.

[11] 4,072,749

[45] Feb. 7, 1978

[54] USE OF IPRONIDAZOLE IN COMBATTING CLOSTRIDIAL INFECTIONS

[75] Inventors: Gian Paolo Maestrone, Staten Island, N.Y.; Milan Mitrovic, Nutley, N.J.

[73] Assignee: Hoffmann-La Roche Inc., Nutley, N.J.

[21] Appl. No.: 691,793

[22] Filed: June 1, 1976

[51] Int. Cl.² .................................... A61K 31/415
[52] U.S. Cl. ........................................ 424/273 R
[58] Field of Search ................................ 424/273

[56] References Cited

PUBLICATIONS

Cavalleri et al., Chem. Abst. vol. 79 (1973), p. 87844f.

Primary Examiner—Sam Rosen
Attorney, Agent, or Firm—Samuel L. Welt; Bernard S. Leon; R. Hain Swope

[57] ABSTRACT

The use of ipronidazole and water-soluble, pharmaceutically acceptable salts thereof in the prevention and treatment of clostridial infections in domestic animals is described.

8 Claims, No Drawings

USE OF IPRONIDAZOLE IN COMBATTING CLOSTRIDIAL INFECTIONS

BACKGROUND OF THE INVENTION

The present invention affords a highly efficacious method for the prevention and treatment of infections wherein the causative organism is one or more species of the Genus Clostridium, anaerobic, spore forming, gram positive bacilli. These organisms have been demonstrated to be the causative agents of black leg, malignant edema, necrotic hepatitis and enterotoxemia in ruminants, particularly cattle and sheep, diseases which are economically damaging to the commercial raisers of these animals.

Ipronidazole is a known compound which chemically is 1-methyl-2-isopropyl-5-nitroimidazole. The preparation of this compound and its pharmaceutically acceptable acid addition salts are described in U.S. Pat. No. 3,634,446 which issued Jan. 11, 1972. In said patent, the compound is disclosed as possessing antiprotozoal and antihistomonal activity, particularly the latter. The compound is described as being especially active in the treatment of the histomonal infection known as turkey blackhead disease or enterohepatitis. Ipronidazole, however, is not recognized in the art as possessing antibacterial activity. Such activity cannot be imputed from U.S. Pat. No. 3,737,546 issued June 5, 1973, which teaches the use of ipronidazole in the prevention and treatment of swine dysentery wherein the causative organism is the large spirochete *Treponema hyodysenteriae*. Another patent, Japanese Pat. No. 7305024, describes mouthwash compositions containing as the active ingredient metronidazole, which is chemically related to ipronidazole and which chemically is 1-(2-hydroxy-ethyl)-2-methyl-5-nitroimidazole. Such compositions are described as possessing strong activity against oral anaerobes such as Peptococcus, Veillonella, Bacteriodes, Fusobacterium and Treponema. The disclosure of the use of this compound locally as a mouthwash is not viewed as suggesting that ipronidazole would be highly efficacious systematically against clostridial infections. Finegold, Proceedings of the 8th International Congress of Chemotherapy, Vol. II (1974) has suggested on the basis of in vitro studies and in vivo work in laboratory animals, that metronidazole may be of value in treating infections wherein the causative organisms are obligately anaerobic bacteria. These limited disclosures are not viewed as suggesting that the active ingredient of the present invention is highly efficacious in the treatment of clostridial infections.

DETAILED DESCRIPTION OF THE INVENTION

According to the present invention, it has been discovered that ipronidazole or pharmaceutically acceptable salts thereof possess unexpectedly high activity in effecting both a cure and prophylaxis against clostridial infections in domestic animals, i.e., cattle, sheep, goats, swine, horses and the like, wherein Clostridia are the causative organism. The method of the invention is particularly concerned with conditions such as black leg and malignant edema in cattle, enterotoxemia in sheep and necrotic hepatitis in ruminants. Ipronidazole is effective in the practice of the invention via oral administration in drinking water and feed and also via parenteral administration, i.e., subcutaneous, intramuscular, intravenous, intraperitoneal or intrarumen injection.

In accordance with the present invention, ipronidazole and pharmaceutically acceptable salts thereof have been found to prevent and effect a cure of clostridial infections when administered in the feed at levels as low as 0.01% by weight. For effective control of clostridial infections, ipronidazole can be administered ad libitum in feed at levels of from about 0.01% by weight to about 0.03% by weight, preferably at about 0.01% by weight to about 0.02% by weight and in drinking water at 0.005% by weight to about 0.015% by weight, preferably about 0.01% by weight. The preferred concentration will depend to some extent on the severity of the infection. Additionally, the method of the invention encompasses the therapeutic treatment of said infections via parenteral administration as will be described hereinafter.

In accordance with the present invention, ipronidazole and pharmaceutically acceptable salts thereof are particularly efficacious in the prevention and therapy of clostridial infections wherein the causative organism is one or more of the following species: *Cl. perfrigens; Cl. novyi; Cl. septicum; Cl. chauvoei;* and *Cl. sordelli*. Infections caused by these organisms are collectively referred to as gas gangrene infections.

The pharmaceutically acceptable salts of ipronidazole in accordance with the present invention include water-soluble acid addition salts with organic and inorganic acids. The preferred salts are those with pharmaceutically acceptable inorganic acids. Most preferred are the hydrochloride and the bisulfate.

The therapeutic compositions of the invention which can be orally administered to the animals can be prepared by directly forming a homogeneous admixture of ipronidazole with a commercial dry feed or ration or by initially forming a concentrate or premix by mixing the active compound with a suitable, non-toxic, edible carrier material. Suitable carrier materials include, for example, corn meal, germ meal or other cereals, soy flour, soya grits, seed meal, oyster shell flour, calcium silicate and the like and may additionally contain other compatible medicaments. A suitable premix can likewise be prepared by admixing the desired quantity of ipronidazole to a measured amount of commercial feed. Premixes in accordance with the invention can advantageously contain from about 1% by weight to about 99% by weight ipronidazole, preferably from about 1% to about 79% by weight, and most preferably about 11% by weight ipronidazole. Such premixes are readily mixed with the feed or ration by techniques conventional in the art.

Where parenteral therapy is contemplated in accordance with the present invention, a single dosage of from 10 mg. to 100 mg., preferably from about 25 mg. to 50 mg. of ipronidazole per kilogram of body weight of the animal to be treated is utilized. A significant response to such parenteral therapy has been demonstrated. The dosage regimen for such therapy will vary according to the age and type of animal, site of infection, severity of infection and the like. For most therapeutic situations, a single daily injection is required for up to four days. It has been demonstrated, however, that up to ten days therapy may be required in the instance of a chronic or significantly advanced infection. Once a remission of symptoms has been observed, it is recommended that the animal as well as others in the herd with which there may have been contact be placed on a prophylactic or therapeutic diet. The extent of parenteral dosage and subsequent diet are considered to be within the discretion of the attending veterinarian.

Parenteral preparations suitable for the practice of the invention are preferably aqueous in nature due to the ability of the ipronidazole to form water-soluble acid addition salts with pharmaceutically acceptable acids. Such preparations may be in reconstitutable powder form and may contain adjunct materials conventional in the art of pharmaceutical compounding such as, for example, preservatives, stabilizers, salts for varying osmotic pressure, buffers and the like. Typical parenteral preparations contain a sufficient amount of a water-soluble acid addition salt of ipronidazole to provide from about 200 mg. to about 2500 mg., preferably from about 1000 mg. to about 1500 mg. of the free base per dose. Such preparations may be in single or multiple dose containers and may be administered intraruminally, intravenously or intraperitoneally.

The following examples further illustrate the invention.

EXAMPLE 1

A total of 6.04 grams of parenteral grade ipronidazole hydrochloride, equivalent to 5.0 grams of free base, was filled into an ampul utilizing a Diehl Meter electric filler or other suitable type filler. The ampuls were sealed and sterilized at 255° F. for 2 hours. Immediately before use this powder is solubilized by the addition of sufficient Water for Injection U.S.P. to achieve a final volume of 50 ml.

EXAMPLE 2

The following example illustrates typical feed supplements suitable for the prevention and treatment of clostridial infections in accordance with the invention.

| Premix: 12 2% | |
|---|---|
| Ingredient | Grams/Kilogram |
| Ipronidazole | 125 |
| Microcel E (Calcium Silicate) | 50 |
| Pulverized Oyster Shell Flour | 825 |

PROCEDURE

The pulverized oyster shell flour was placed in a suitable mixer and, while mixing, the Microcel E was slowly added. After the addition of Microcel E was completed and with continued mixing the ipronidazole was slowly added after which mixing was continued until the mass was homogeneous. The addition of this premix to commercial feed at a rate of 1¾ pounds/ton yields a concentration of ipronidazole of 100 gm. per ton. Such commercial feeds may contain other nutritional or medicinal agents if such are compatible with ipronidazole.

| Premix: 22% | |
|---|---|
| Ingredient | Grams/Kilogram |
| Ipronidazole | 220 |
| Microcel E | 80 |
| Soy Oil | 10–50 |
| Soy meal run (toasted, extracted, milled soy) | 650–690 |

| Premix: 11% | |
|---|---|
| Ingredient | Grams/Kilogram |
| Ipronidazole | 110 |
| Microcel E | 40 |
| Soy Oil | 10–100 |
| Ground Rice Hulls | 750–840 |

PROCEDURE

A portion of the soy meal run (or ground rice hulls) was placed in a suitable mixer and about 10 grams (or 1% by weight of the final mixture) of the soy oil and the Microcel E slowly added thereto and the whole thoroughly mixed. The purpose of the oil is to minimize dust and maintain the mixture in a slightly moist condition during mixing. Therefore, sufficient oil is utilized to so maintain the mixture and the amount of soy meal run (or ground rice hulls) added to the mixture to bring it to final weight is adjusted in terms of the amount of oil utilized. The ipronidazole was then added with mixing and the whole thoroughly mixed until homogeneous. The required amount of additional grain was then added to bring the final weight of the mixture to one kilogram and the whole again mixed until homogeneous.

These premixes when combined with commercial feeds at the rate of 2 pounds per ton yield a concentration per ton of 200 Gm. and 100 Gm. ipronidazole, respectively.

EXAMPLE 3

The activity of ipronidazole against *Cl. perfringens* was demonstrated in vitro as follows: A 48-hour bacterial growth of various strains of *Cl. perfringens* was swabbed onto the surface of 5% bovine blood Mueller-Hinton agar plates on which 6.3 mm discs, containing various concentrations ipronidazole were placed. The plates were then incubated under anaerobic conditions at 37° C. for 48 hours. The diameter of the zone of inhibition around the disc was then measured and is expressed in millimeters. The results are set forth in the following table.

Table

| Compound | Disc Potency (mcg.) | Zone of Inhibition (diameter in mm) Strain of Cl. Perfringens 651 | 656 |
|---|---|---|---|
| Irponidazole | 2.5 | >25 | >25 |
| " | 1.2 | 22 | 24 |
| " | 0.6 | 20 | 18 |

EXAMPLE 4

The preventive activity of ipronidazole was demonstrated in vivo as follows: Male, albino mice weighing approximately 20 grams were inoculated subcutaneously with a 0.1 ml. inoculum medium and properly titrated ($7.1 \times 10^8$ organism). This inoculation produced a lethal effect in untreated (control) mice.

Groups of ten mice, dosed with organism, were fed various levels of ipronidazole in the feed beginning 24 hours pre-infection. The feed was continued for seven days. Observations were made at the termination of medication (7 days) and 7 days thereafter. The results are expressed in Table 1 below in terms of percent mortality.

Table 1

| Percent Concentration of Ipronidazole | Percent Mortality Treatment Begun 24 hours Pre-Infection | |
|---|---|---|
| | Day 7 | Day 14 |
| 0.03 | 0 | 0 |
| 0.02 | 0 | 0 |
| 0.01 | 35 | 35 |
| 0.005 | 60 | 60 |
| 0 (Control) | 60 | 60 |

The results given above indicate that ipronidazole is highly effective in dose ranging from 0.03% to about 0.0% by weight in feed.

EXAMPLE 5

Therapeutic efficacy of ipronidazole by parenteral administration *Cl. novyi* was demonstrated as follows: Groups of mice infected with *Cl. novyi* in the manner described in Example 4 were treated with a single subcutaneous injection of various dosages of ipronidazole one day after infection. The minimum effective dosage was calculated to be 25 mg./kg. The effectiveness of this dosage was 95% one week post-inoculation and 98% two weeks post-inoculation based on reduction of clinical signs.

We claim:

1. A method for the treatment of clostridial infections in ruminants which comprises orally administering to animals afflicted therewith feed or drinking water containing from about 0.005% by weight to about 0.03% by weight of a substance selected from the group consisting of ipronidazole and pharmaceutically acceptable acid addition salts thereof.

2. The method of claim 1 wherein said substance is ipronidazole and administration is via the feed, said feed containing from about 0.01% by weight to about 0.03% by weight of said substance.

3. The method in accordance with claim 2 wherein said feed contains about 0.02% by weight ipronidazole.

4. The method of claim 1 wherein said substance is ipronidazole hydrochloride and administration is via the drinking water, said drinking water containing from about 0.005% by weight to about 0.015% by weight of said substance.

5. The method in accordance with claim 4 wherein said drinking water contains about 0.015% by weight ipronidazole hydrochloride.

6. A method for the therapeutic treatment of clostridial infections in ruminants which comprises parenterally administering to animals afflicted therewith a composition containing from about 10 mg. to about 100 mg. of a substance selected from the group consisting of ipronidazole and pharmaceutically acceptable salts thereof per kilogram of body weight of said animal.

7. The method of claim 5 wherein said composition contains from about 25 mg. to about 50 mg. of said substance per kilogram of body weight of said animal.

8. The method of claim 5 wherein said substance is ipronidazole hydrochloride.

* * * * *